United States Patent [19]

Schleppnik

[11] 4,187,251

[45] Feb. 5, 1980

[54] MALODOR COUNTERACTANTS

[76] Inventor: Alfred A. Schleppnik, No. 1 Hanley Downs, St. Louis, Mo. 63117

[21] Appl. No.: 908,423

[22] Filed: May 22, 1978

Related U.S. Application Data

[63] Continuation-in-part of Ser. No. 771,753, Dec. 16, 1976, abandoned.

[51] Int. Cl.² .............................................. C07C 49/43
[52] U.S. Cl. .................................. 260/586 R; 424/76
[58] Field of Search .................................. 260/586 R

[56] References Cited

PUBLICATIONS

Pishnamazzade et al., "C.A."76: 139986p (1972).
Pishnamazzade et al., "C.A."74: 53119e (1971).
Heymes et al., "Ann. Chim (Paris)", 1968+ 3, pp. 543–554.
Cantrell, "J. Org. Chem.", 32(5), pp. 1669–1672 (1967).
Groves et al. "J. Chem. Soc. C", 1968(17), 2215–2217.

*Primary Examiner*—Norman Morgenstern

[57] ABSTRACT

The compounds represented by the structural formula

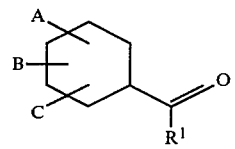

wherein
A, B and C each independently represent hydrogen or lower alkyl having from 1 to 4 carbon atoms, provided that the sum of the carbon atoms in A, B and C is no more than 5,
$R^1$ represents alkyl having from 1 to 4 carbons, have been found to be particularly useful in compositions and methods for counteracting malodors. Novel compounds are also disclosed.

2 Claims, No Drawings

4,187,251

MALODOR COUNTERACTANTS

CROSS-REFERENCES TO RELATED APPLICATIONS

This application is a continuation-in-part of application Ser. No. 771,753, filed Dec. 16, 1976, now abandoned.

FIELD OF THE INVENTION

This invention relates to the art of treatment of offensive odors, more particularly, to compositions and methods to counteract certain malodors.

DESCRIPTION OF THE PRIOR ART

The art of perfumery began, perhaps in the ancient cave dwellings of prehistoric man. From its inception, and until comparatively recently, the perfumer has utilized natural perfume chemicals of animal and vegetable origin. Thus, natural perfume chemicals such as the essential oils, for example, oil of rose and oil of cloves, and animal secretions such as musk, have been manipulated by the perfumer to achieve a variety of fragrances. In more recent years, however, research perfume chemists have developed synthetic materials having characteristics particularly desired in the art. These synthetic aroma chemicals have added a new dimension to the ancient art of the perfumer, since the compounds prepared are usually of a stable chemical nature, are inexpensive as compared with the natural perfume chemicals and lend themselves more easily to manipulation than the natural perfume chemicals since such natural perfume chemicals are usually a complex mixture of substances which defy chemical analysis. In contrast thereto, the synthetic aroma chemicals possess a known chemical structure and may therefore be manipulated by the perfumer to suit specific needs. Such needs vary over a very wide spectrum. Accordingly, there is a great need in the art of fragrance compositions for compounds possessing specific olfactory characteristics.

Heretofore a major effort in the art of perfumery has been directed to providing means of treating odors that are offensive to the human sense of smell. Such odors encompass a variety of odors such as bathroom-odor, kitchen-odor, body-odor, cigar smoke-odor, etc. Many products have been developed in an attempt to overcome these odors. So-called "room fresheners" or "room deodorants" are illustrative of such products.

In general these products have provided a masking effect by one of two mechanisms. The maskant fragrance is provided either to suppress the offensive odor by providing a more pleasing aroma in large quantities or by providing an aroma that blends with the offensive odor to provide a different and more desirable aroma. Unfortunately, in both instances a large amount of fragrance must be utilized which in itself often proves to be offensive. Furthermore, the offensive odor is usually still detectable at the levels of maskant fragrances that are reasonably tolerable. Accordingly, compositions and methods for counteracting such offensive odors which would substantially eliminate such odors without the above-noted disadvantages are particularly desirable.

Particularly noxious odors are caused by compounds which have a pronounced tendency to either donate or accept protons. Such compounds will hereinafter be referred to as "malodors." They include the olfactory notorious classes of lower carboxylic acids, thiols, thiophenols, phenols, lower amines, phosphines and arsines.

The compounds 4-cyclohexyl-4-methyl-2-pentanone has heretofore been found to possess the ability to counteract such malodors.

The following compounds have been described in the literature:
cyclohexyl methyl ketone—R. P. Mariella & R. R. Raube, JACS 74; 518 (1952)
cyclohexyl ethyl ketone—C. Hell & O. Schaal, Ber. 42; 2230 (1909)
cyclohexyl isopropyl ketone—E. P. Burrows, F. J. Welch & H. S. Mosher, JACS 82; 880 (1960)
cyclohexyl n-propyl ketone—G. Darzens & H. Rost, Compt. rend. 153; 772 (1911)
cyclohexyl n-butyl ketone—E. P. Burrows, F. J. Welch & H. S. Mosher, JACS 82; 880 (1960)
2-methylcyclohexyl methyl ketone—A. Heymes, M. Dvolaitzky & J. Jacques, Ann. chim. (Paris) 3; 543 (1968)
3-methylcyclohexyl methyl ketone—M. Mousseron, R. Granger & J. Claret, Bull. so. chim., 598 (1947)
4-methylcyclohexyl methyl ketone—N. Duford & E. Flamand, Canad. J. Chem. 46, 1073 (1968)

SUMMARY OF THE INVENTION

The present invention provides compounds and compositions which are especially useful in view of their ability to counteract malodors. Furthermore, novel methods are provided, i.e. the use of such compounds and compositions to counteract malodors. Still further, certain of these compounds are novel.

The compounds which exhibit this surprising ability to counteract malodors are represented by the following structural formula:

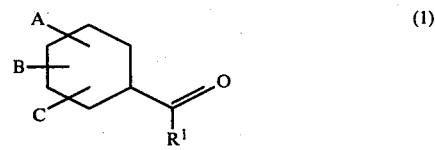

wherein
A, B and C each independently represent hydrogen, a lower alkyl having from 1 to 5 carbon atoms (preferably from 1 to 4 carbons or from 1 to 3 carbons), provided that the sum of the carbon atoms in A, B and C is no more than 7 (preferably no more than 6, especially no more than 5), and
$R^1$ represents an alkyl having from 1 to 6 carbon atoms (preferably from 1 to 5, especially from 1 to 4).

In the above formula, especially preferred are those compounds wherein A, B and C independently represent hydrogen, methyl, ethyl or propyl; the sum of the carbon atoms in A, B and C is no more than 5 and $R^1$ represents methyl, ethyl, propyl or butyl.

DESCRIPTION OF THE PREFERRED EMBODIMENTS

The term "counteract" as used herein means the effect on the human sense of smell and/or the malodor resulting in alleviating the offensiveness of the malodor to the human sense of smell. It is not intended that this term be limited to any particular mechanism by which such a result may be obtained.

The compounds useful in this invention can preferably be prepared as illustrated by the following equation:

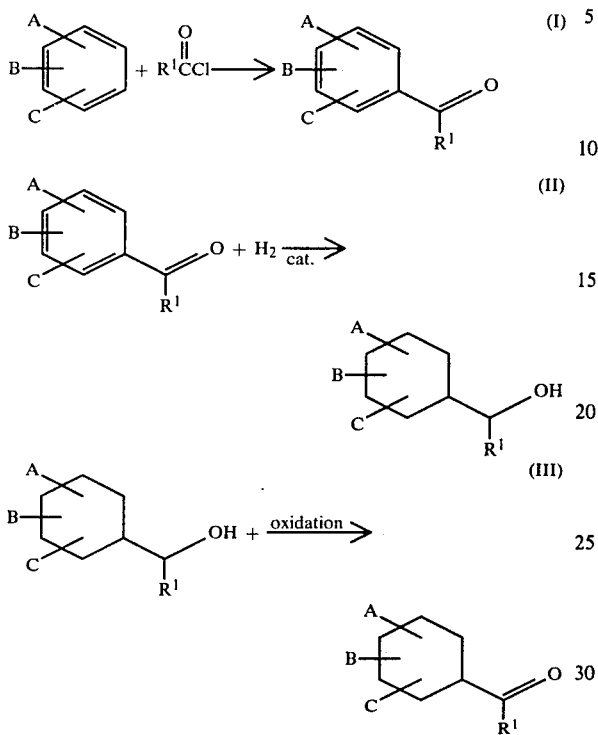

In the above equations, A, B, C and $R^1$ have the same meanings as set forth above.

As shown in equation (I) a substituted or unsubstituted benzene is acylated, preferably under Friedel-Crafts conditions, with an acyl chloride to form the corresponding phenyl-alkyl ketone. As shown in equation (II) this phenyl-alkyl ketone is hydrogenated over a suitable catalyst, preferably a rhodium metal-containing catalyst, to form the corresponding alkylated cyclohexyl-methanol. Oxidation of this alcohol, for instance by the Brown/Garg-modification with chromic acid, forms the desired ketone as shown in equation (III).

The instant compounds are capable of effectively counteracting malodors when utilized in small quantities and in many different mediums. For instance, use in room fresheners or room deodorants in the form of aerosols (sprays, etc.), liquids (wick type), solids (wax bases as in pomander, plastics, etc.), powders (sachets, dry sprays) and gels (solid gel sticks) are particularly preferred. Other illustrative uses are in clothes deodorants as applied by washing machine applications such as in detergents, powders, liquids, whiteners or fabric softeners or by other applications such as closet blocks, closet aerosol sprays, or clothes storage areas or in dry cleaning to overcome residual solvent notes on clothes; in bathroom accessories such as paper towels, bathroom tissues, sanitary napkins, towellets, disposable wash cloths, disposable diapers, and diaper pail deodorants; in cleansers such as disinfectants and toilet bowl cleaners; in cosmetic products such as antiperspirant and underarm deodorants, general body deodorants in the form of powders, aerosols, liquids or solid, or hair care products such as hair sprays, conditioners, rinses, hair colors and dyes, permanent waves, depilatories, hair straighteners, hair groom applications such as pomade, creams, lotions, etc., medicated hair care products containing such ingredients as S-Selenium-sulfide, coal tar, salicylates, etc., or shampoos, or foot care products such as foot powders, liquids or colognes, after shaves and body lotions, or soaps and synthetic detergents such as bars, liquids, foams or powders; in odor control such as during manufacturing processes, such as in the textile finishing industry and the printing industry (inks and paper); in effluent control such as in processes involved in pulping, stock yard and meat processing, sewage treatment, or garbage disposal, or in product odor control as in textile finished goods, rubber finished goods, car fresheners, etc.; in agricultural and pet care products such as dog and hen house effluents, and domestic animal and pet care products such as deodorants, shampoo or cleaning agents, or animal litter materials; in large scale closed air systems such as auditoriums, and subways and transport systems.

The amount of any such compound to be utilized has been found to be independent, in general, of the particular malodor involved. Likewise, the concentration of the malodor in the air containing it has been found to not effect the effective amount of the compound utilized. An amount effective to counteract the malodor should be used. The amount of any such compound however depends on the medium in which the compound is used, the temperature, humidity, air volume and air circulation. In general, such compounds are effective when present in air (containing the malodor) at levels as low as 0.01 mg./cubic meter of air. Of course, depending on the structure of the particular compound used, some compounds are more active than others. Any concentration above this amount will generally be effective. However, from a practical point of view, more than about 1.0 to 2.0 mg./cubic meter of air is probably unnecessary.

Novel compounds useful in the present invention are 4-ethylcyclohexyl methyl ketone and 4-isopropylcyclohexyl methyl ketone.

Particularly preferred compounds useful in the instant invention are cyclohexyl methyl ketone and 3-methylcyclohexyl methyl ketone.

Other illustrative compounds useful in the present invention are:
4-tert.-butylcyclohexyl methyl ketone
2-methyl-4-tert.butylcyclohexyl methyl ketone
2-methyl-5-isopropylcyclohexyl methyl ketone
4-methylcyclohexyl isopropyl ketone
4-methylcyclohexyl sec.butyl ketone
4-methylcyclohexyl isobutyl ketone
2,4-dimethylcyclohexyl methyl ketone
2,3-dimethylcyclohexyl methyl ketone
2,2-dimethylcyclohexyl methyl ketone
3,3-dimethylcyclohexyl methyl ketone
4,4-dimethylcyclohexyl methyl ketone
3,3,5-trimethylcyclohexyl methyl ketone
2,2,6-trimethylcyclohexyl methyl ketone The following examples are given to illustrate the instant invention in detail. It is to be understood that the specific details given in the examples are not to be construed as limiting the scope of the invention. The symbol "mg./cu. meter" refers to the weight (in milligrams) of material present in one cubic meter of air.

EXAMPLE 1

Cyclohexyl Methyl Ketone

Cyclohexyl methyl ketone is formed in small amounts as a by-product in the hydrogenation of acetophenone to 1-cyclohexyl ethanol. Purification of the 1-cyclohexyl ethanol by fractionation produces a cyclohexyl methyl ketone enriched forerun which also contains 1-cyclohexyl ethanol. A typical forerun containing 38.5 g. (0.3 moles) of 1-cyclohexyl ethanol and 21.3 g. (0.1688 moles) of cyclohexyl methyl ketone was diluted with 200 ml. of acetone, chilled in an ice bath and oxidized with 75 ml. of 8 N chromic acid in 8 N sulfuric acid (JONES REAGENT) at 15°–20° C.

Isolation was carried out by decanting the upper organic layer and concentrating on a rotatory evaporator. The heavy chromium sulfate solution was diluted with water and extracted with ether. To this extract the concentrate from the evaporator was added. The resulting ether solution was washed thoroughly with water, concentrated sodium bicarbonate solution and brine and evaporated on the rotatory evaporator to give 53.4 g. of cyclohexyl methyl ketone—having a chemical, fruity fragrance (99.35% pure by GLC). $n_D^{25} = 1.4500$. The NMR-spectrum had two broad multiplets at 1.33 and 1.73 ppm. (cyclohexyl protons) and a singlet at 2.00 ppm. indicating the

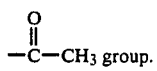

group.

EXAMPLE 2

Cyclohexyl Ethyl Ketone

To a solution of 21.4 g. (0.15 moles) of 1-cyclohexyl-1-propanol in 150 ml. of ether was added, with stirring and cooling in an ice bath, 75 ml. of 2 N chromic acid (BROWN GARG-Reagent) at such a rate as to maintain the temperature at 15°–20° C. After the addition was complete the ice bath was removed and stirring continued for 30 min. IR- and GLC-analysis confirmed that all starting material had been consumed.

Isolation procedures similar to those described in Example 1 gave 19.4 g. of crude cyclohexyl ethyl ketone, $n_D^{25} = 1.4508$. It contained a small amount of low boiling impurities which were removed by distillation through a short Vigreux-column. After a forerun of 0.9 g. (b.p. 60°–62° C./5 mm. Hg, $n_D^{25} = 1.4500$) the product, cyclohexyl ethyl ketone, was collected at b.p. 62° C./5 mm. Hg. as a colorless fragrant (powerful, chemical) liquid. It had $n_D^{26} = 1.4506$ (purity 99.2% by GLC). Yield—15.5 g. (73.7%).

EXAMPLE 3

Cyclohexyl Isopropyl Ketone

A forerun obtained in the fractionation of technical grade 1-cyclohexyl-2-methyl-1-propanol consisting of 8.15 g. of cyclohexyl isopropyl ketone and 17.85 g. (0.1142 moles) of 1-cyclohexyl-2-methyl-1-propanol was dissolved in 120 ml. of ether and treated at 15°–20° C. with 58 ml. 2 N chromic acid solution (BROWN GARG-Reagent). The oxidation was complete after 30 minutes.

Isolation procedures similar to those described in Example 1 gave 25.7 g. of crude cyclohexyl isopropyl ketone, $n_D^{23} = 1.4489$ which was essentially pure. Traces of low boiling impurities were removed by distillation through a short Vigreux-column. After a forerun of 2.2 g. (b.p. 35°–38° C./0.8 mm. Hg., $n_D^{23} = 1.4475$) the cyclohexyl isopropyl ketone was collected at b.p. 38° C./0.8 mm. Hg. as a colorless fragrant (green, spicy, minty) liquid, $n_D^{23} = 1.4490$. Yield—22.7 g. (82.6%) having a purity of 99.6% by GLC.

EXAMPLE 4

Cyclohexyl n-Propyl Ketone

A forerun obtained in the fractionation of technical grade 1-cyclohexyl-1-butanol consisting of 15.0 g. (0.096 moles) 1-cyclohexyl-1-butanol and 15.5 g. (0.101 moles) cyclohexyl n-propyl ketone was dissolved in 150 ml. of ether and oxidized with 50 ml. (0.1 mol) of 2 N chromic acid (BROWN GARG-Reagent) at 10°–15° C. The reaction was fast, highly exothermic and practically quantitative.

Isolation procedures similar to those described in Example 1 (including one additional wash of the ether solution containing the crude ketone with sodium bicarbonate solution to remove a dark amber color) gave 29.7 g. of crude cyclohexyl n-propyl ketone. Yield—96.3%, $n_D^{23} = 1.4505$. Distillation through a short Vigreux-column gave a forerun of 2.8 g. (b.p. 30°–38° C./0.8 mm. Hg., $n_D^{24} = 1.4454$) and the cyclohexyl n-propyl ketone was collected as a colorless fragrant (green, chemical, ethereal) liquid at b.p. 38°–44° C./0.8 mm. Hg. which was almost pure by GLC analysis. $n_D^{24} = 1.4515$. Yield—25.7 g. (83.3%).

EXAMPLE 5

Cyclohexyl n-Butyl Ketone

A solution of 13.7 g. (0.08 moles) 1-cyclohexyl-1-pentanol in 40 ml. of ether was oxidized with 40 ml. 2 N chromic acid solution (BROWN GARG-Reagent) at 15°–20° C.

Isolation procedures similar to those described in Example 1 gave 12.11 g. of crude cyclohexyl n-butyl ketone. During fractionation through a Holtzmann-column a center cut (b.p. 105° C./9 mm. Hg.) was collected which was 1-cyclohexyl n-butyl ketone was obtained as a colorless fragrant (balsamic woody) liquid, $n_D^{25} = 1.4538$. Yield—8.2 g.

EXAMPLE 6

2-Methylcyclohexyl Methyl Ketone

A solution of 13.2 g. (0.0928 moles) cis/trans-1-(2-methylcyclohexyl)-1-ethanol in 50 ml. of ether was chilled in an ice bath and 50 ml. 2 N chromic acid solution (BROWN GARG-Reagent) was added dropwise, with stirring, at such a rate as to maintain the temperature at about 10° C. After the addition was complete, the ice bath was removed and the stirring was continued at ambient temperature for one hour.

Isolation procedures similar to those described in Example 4 gave 9.95 g. of crude 2-methylcyclohexyl methyl ketone as a colorless liquid (76.4%) which was purified by distillation through a short Vigreux-column. 2-methylcyclohexyl methyl ketone was collected as a center cut (b.p. 72° C./8 mm. Hg., $n_D^{25} = 1.4552$). It was a colorless fragrant (minty, fresh, chemical) liquid. Yield—8.55 g. (65.8%).

EXAMPLE 7

3-Methylcyclohexyl Methyl Ketone

A solution of 13.2 g. (0.0928 moles) cis/trans-1-(3-methylcyclohexyl)-1-ethanol in 50 ml. ether was oxidized with 52 ml. 2 N chromic acid solution (BROWN GARG-Reagent) and isolated as described in Example 6. 101.6 g. 3-methylcyclohexyl methyl ketone was obtained (77.6%) having a 96% purity by GLC. It was purified by distillation through a short Vigreux-column to give a substantially pure cis-trans-3-methylcyclohexyl methyl ketone as a colorless fragrant (ethereal, chemical harsh) liquid (b.p. 59° C./100 mm. Hg., $n_D^{25}$=1.4489). Yield—7.13 g. (54.9%).

EXAMPLE 8

4-Methylcyclohexyl Methyl Ketone

A solution of 14.4 g. (0.1014 moles) cis/trans-1-(4-methylcyclohexyl)-1-ethanol in 50 ml. of ether was oxidized with 52 ml. 2 N chromic acid solution and isolated as described in Example 6. The crude 4-methylcyclohexyl methyl ketone was obtained in a yield of 12.0 g. (84.0%) with a 99.0% purity by GLC. Takeover distillation gave 9.1 g. (64.1%) of 4-methylcyclohexyl methyl ketone (b.p. 54° C./9.5 mm. Hg., $n_D^{25}$=1.4500) as a colorless fragrant (fresh, green, powerful) liquid.

EXAMPLE 9

4-Ethylcyclohexyl Methyl Ketone

A solution of 15.9 g. (0.1019 moles) cis/trans-1-(4-ethylcyclohexyl)-1-ethanol in 50 ml. ether was oxidized with 50 ml. 2 N chromic acid solution (BROWN GARG-Reagent) and isolated as described in Example 6. The crude product (16.2 g.=103%) was purified by distillation over 0.133 g. boric acid. Substantially pure cis/trans-4-ethylcyclohexyl methyl ketone (b.p. 91° C./95 mm. Hg., $n_D^{25}$=1.4541). It was a colorless fragrant (chemical, pungent) liquid.

EXAMPLE 10

4-Isopropylcyclohexyl Methyl Ketone

A solution of 15.1 g. (0.0887 moles) cis/trans-1-(4-isopropylcyclohexyl)-1-ethanol in 50 ml. of ether was oxidized with 50 ml. of a 2 N chromic acid solution (BROWN GARG-Reagent) and isolated as described in Example 6 to give 14.15 g. crude cis/trans-4-isopropylcyclohexyl methyl ketone. Yield—95.7%. This product was purified by distillation through a short Vigreux-column. The recovered 4-isopropylcyclohexyl methyl ketone, a colorless fragrant (green, pungent, camphor) liquid, had a b.p. 59°-60° C./0.8 mm. Hg., $n_D^{25}$=1.4573.

EXAMPLE 11

The following malodor concentrate was prepared:

| Bathroom Malodor Concentrate | |
| --- | --- |
| Component | Parts by Wt. |
| skatole | 0.91 |
| β-thionaphthol | 0.91 |
| 95% aqueous solution of thioglycolic acid | 21.18 |
| n-caproic acid | 6.00 |
| p-cresyl isovalerate | 2.18 |
| N-methyl morpholine | 6.00 |
| dipropylene glycol | 62.82 |

Aerosol cans were prepared with the above malodor with the following concentrations:

| Bathroom Malodor Aerosol | |
| --- | --- |
| Component | Parts by Wt. |
| Bathroom Malodor Concentrate | 0.1 |
| dipropylene glycol | 4.9 |
| Propellant | |
| a. trichloromonofluoromethane | 47.5 |
| b. dichlorodifluoromethane | 47.5 |

A "Spice for Cologne" fragrance was selected for use in testing the malodor counteractant ability of exemplary compounds. The "Spice for Cologne" fragrance contained the following ingredients:

| Ingredients | Parts by Wt. |
| --- | --- |
| Lavandin Abrialis Oil | 60 |
| Amyl Cinnamic Aldehyde | 20 |
| Amyl Salicylate | 150 |
| Benzyl Acetate | 30 |
| Linalool | 30 |
| Cedarwood Oil | 10 |
| Geraniol | 130 |
| Isopulegol | 60 |
| Methyl Anthranilate (10% by wt. solution in dipropylene glycol) | 20 |
| Musk Xylol | 60 |
| Coumarin | 50 |
| Phenyl Ethyl Acetate | 30 |
| Terpinyl Acetate | 100 |
| Cinnamon Leaf Oil | 40 |
| Petitgrain Oil SA | 60 |
| Ylang ylang Oil | 130 |
| Phenyl Acetaldehyde Dimethyl Acetal | 15 |
| Cinnamic Alcohol | 5 |
| | 1000 |

Aerosol cans were prepared with the above fragrance composition containing the compounds indicated in Table 1 as follows:

| Component | % by Wt. |
| --- | --- |
| "Spice for Cologne" fragrance | 0.45 |
| Compound to be tested | 0.05 |
| Propellant | |
| a. trichlormonofluoromethane | 49.75 |
| b. dichlorodifluoromethane | 49.75 |
| | 100.00 |

A test chamber having inside dimensions of 3.35×3.66×2.44 (meters) with a total volume of 29.9 cubic meters, having an access door and an exhaust fan was provided. The capacity of the exhaust fan was 14 cu. meters/min. In order to insure satisfactory evacuation, the exhaust fan was operated for five minutes between tests and an olfactory check was made to determine if any residual odor could be detected prior to conducting the next test.

After the test chamber had been suitably evacuated, the bathroom malodor was sprayed from the aerosol can for about five seconds. After a delay of from 10–15 seconds, the fragrance composition aerosol was sprayed for about five seconds (five seconds being an average time such an aerosol would usually be used by a housewife). One minute thereafter a 2 member panel (consisting of 1 person skilled in perfumery and odor evaluation and 1 person having so such skills but being familiar with fragrances in general) entered the test chamber, performed an olfactory evaluation for detection of the malodor and recorded their observations. All tests were performed with neither member of the panel being aware of the identity of the material being tested.

Based on the flow rate through the valve utilized in the aerosol can the approximate amount of aerosol, containing the bathroom malodor concentrate, introduced into the test chamber is 267 mg./cu. meter.

The amount of aerosol containing the fragrance compositions introduced into the test chamber is approximately 260 mg./cu. meter.

Using the above test procedure, the compounds indicated in Table 1 were tested for their ability to counteract the bathroom malodor. The results are shown in Table 1.

TABLE 1

| Compound of Example | Activity+ | Comments |
| --- | --- | --- |
| 1 | U* | Very fresh, pungent, powerful |
| 2 | U | Very fresh, pungent, irritating |
| 3 | U | Very fresh, extremely light residual |
| 4 | V | Pungent, slightly irritating |
| 5 | V | Pungent, heavy background |
| 6 | V | Clean fresh light |
| 7 | U* | Very nice, very light residual |
| 8 | U | Very clean, very light residual |
| 9 | V | Pungent, no malodor, heavy residual |
| 10 | VU | Pungent, sharp, nice clean |

+ Ability of compound to counteract the malodor according to the following scale:
U* "Outstanding" - Fresh air effect pronounced and producing extremely light or no residual odor at all.
U "Excellent" - Fresh air effect and light and pleasant residual background odor.
V "Very good" - No fresh air effect but total abatement of malodors, variable, but not high residual background odor.
W "Good" - Only traces of malodor, often of changed quality, remain. Residual background odor acceptable to pleasant, not too strong.
X "Fair" - Original malodor clearly discernable but of low intensity. Residual background odor acceptable at best.
Y "Poor" - Original malodor somewhat reduced in intensity, but dominates. Overall residual background odor unpleasant to unacceptable.
Z "No activity".

While the invention has been described herein with regard to certain specific embodiments, it is not so limited. It is to be understood that variations and modifications thereof may be made by those skilled in the art without departing from the spirit and scope of the invention.

The embodiments of this invention in which an exclusive property or privilege is claimed are defined as follows:

1. 4-ethylcyclohexyl methyl ketone.
2. 4-isopropylcyclohexyl methyl ketone.

* * * * *